(12) United States Patent  (10) Patent No.: US 8,828,231 B2
Schon et al.  (45) Date of Patent: Sep. 9, 2014

(54) METHOD FOR RECOVERING CARBOXYLIC ACIDS FROM DILUTE AQUEOUS STREAMS

(75) Inventors: Steven G. Schon, Strafford, PA (US); Cecile V. Bertrand, Bagnois (FR)

(73) Assignee: Arkema Inc., King of Prussia, PA (US)

( * ) Notice: Subject to any disclaimer, the term of this patent is extended or adjusted under 35 U.S.C. 154(b) by 328 days.

(21) Appl. No.: 13/060,083

(22) PCT Filed: Aug. 27, 2009

(86) PCT No.: PCT/US2009/055100
§ 371 (c)(1),
(2), (4) Date: Feb. 22, 2011

(87) PCT Pub. No.: WO2010/027879
PCT Pub. Date: Mar. 11, 2010

(65) Prior Publication Data
US 2011/0147307 A1   Jun. 23, 2011

Related U.S. Application Data

(60) Provisional application No. 61/093,840, filed on Sep. 3, 2008.

(51) Int. Cl.
B01D 11/04   (2006.01)
C07C 45/80   (2006.01)
C07C 51/48   (2006.01)
B01D 3/00    (2006.01)

(52) U.S. Cl.
CPC ............... *C07C 51/48* (2013.01); *C07C 45/80* (2013.01)
USPC .......................................... 210/639; 210/634

(58) Field of Classification Search
None
See application file for complete search history.

(56) References Cited

U.S. PATENT DOCUMENTS

| 3,534,091 A | 10/1970 | Hartel et al. |
| 4,353,784 A * | 10/1982 | Koga et al. .................. 203/16 |
| 4,433,181 A * | 2/1984 | Holter ......................... 568/750 |
| 6,166,248 A | 12/2000 | Heida et al. |
| 6,281,386 B1 | 8/2001 | Fauconet et al. |
| 6,555,707 B1 | 4/2003 | Nestler et al. |
| 2007/0106093 A1 | 5/2007 | Fauconett et al. |
| 2008/0183014 A1 | 7/2008 | Diefenbacher et al. |

* cited by examiner

*Primary Examiner* — Katherine Zalasky
(74) *Attorney, Agent, or Firm* — Steven D. Boyd

(57) ABSTRACT

Improvement in separating lower, C2 saturated and/or C3, and/or C4, saturated and/or unsaturated mono carboxylic acids from aqueous streams via extraction by using as the extractant an organic acid or ester or mixtures thereof with a melting point below 10° C., a normal boiling point between 190 and 280° C. and a Hildebrand solubility parameter between 8 and 11 $cal^{1/2}\ cm^{-3/2}$.

6 Claims, 2 Drawing Sheets

METHOD FOR RECOVERING CARBOXYLIC ACIDS FROM DILUTE AQUEOUS STREAMS

BACKGROUND OF THE INVENTION

1. Field of the Invention

The present invention relates to a method for recovering carboxylic acids from dilute aqueous streams by extraction with high-boiling organic acid or ester solvents and concentration. More particularly, the present invention relates to a method for recovering acrylic acid from dilute acid water streams in processes for the manufacture of acrolein or acrylic acid.

2. Discussion of the Prior Art

Both acrolein and acrylic Acid (AA) are conventionally produced by gas-phase catalytic oxidation of propylene. There are also reports in the patent and open literature that with suitable catalysts, propane can be used as a feedstock lieu of propylene.

In acrolein manufacture, the reaction is typically carried out in a single-stage reactor, optimized to selectively oxidize propylene to acrolein, with a minimum of byproducts. However, some over-oxidation occurs resulting in the production of AA as well. In AA manufacture, the reaction is typically carried out in two stages, oxidizing propylene to acrolein in the first stage (as in acrolein manufacture), and then further oxidizing the acrolein to AA in the second stage.

In both acrolein and AA manufacture, AA is first separated from the gas phase reactor effluent by absorption into water, resulting in a dilute aqueous AA stream that also contains water-soluble, medium- and higher-boiling reaction byproduct impurities such as acetone, allyl alcohol, acetic acid, propionic acid, and maleic acid.

In AA manufacture, the aqueous AA stream leaving the absorber typically contains less than 40-65% AA. This crude aqueous AA stream is sent to a purification system, which typically involves a series of energy-intensive distillation columns.

Because of the relatively high water content, and the fact that AA forms azeotropes with water and other reaction impurities, the AA purification system is complex and energy intensive.

In acrolein manufacture, the aqueous AA stream leaving the absorber typically contains less than 10% AA; at standalone manufacturing sites, it is handled as a waste. Although dilute in AA, the concentrations are sufficiently high to make it impractical to treat the wastewater by relatively low-cost means such as biological treatment or wet-air oxidation. Thus, the AA wastewater is typically sent to an incinerator. Operating the incinerator requires a large amount of fuel owing to the large amount of water present, relative to the AA. Thus, handling and incineration of the dilute AA stream represents a significant operating expense in the manufacture of acrolein. While in principle the aqueous AA could be transported to an off-site AA manufacturing facility for recovery of the AA, the dilute AA concentration makes transportation costs prohibitive.

In the case of acrolein manufacture, it would be desirable to separate and recover AA from the dilute wastewater stream, yielding an AA concentrate, and an AA-depleted wastewater. The AA concentrated could be transported economically to an off-site AA manufacturing facility, for purification of the AA into a commercially valuable product. The AA-depleted wastewater may have a sufficiently low concentration of residual organic compounds, so that it can be feasibly treated by less expensive means than incineration, e.g. biological wastewater treatment or wet-air oxidation.

In case of AA manufacture, it would be desirable to separate the AA from the water in crude AA exiting the absorber. Reducing the water loading in the crude AA sent to purification reduces the energy requirements and costs in the distillation train.

The prior art describes various extraction-based processes for separating carboxylic acids, especially AA, from aqueous streams. However, most of these involve solvents that boil relatively close to or below the boiling point of the carboxylic acids of interest, especially AA, and are primarily intended for use with concentrated aqueous carboxylic acid streams. Separation of the carboxylic acid from the solvents generally requires complex and energy-intensive distillations. As the typical solvents generally are boiled overhead, the carboxylic acids are taken as the bottoms streams, exposing them to high temperatures that can degrade the product.

In order to avoid taking the carboxylic acids as bottom streams, the alternative is to use solvents which are less volatile, i.e. high-boiling, than the carboxylic acids, as the carboxylic acids are boiled overhead, and the solvent generally is taken as the bottoms streams. The fouling tendency can be further mitigated by reducing the pressure of the distillations, and/or the addition of polymerization inhibitors to the distillation system. This is well known in the art.

Prior art related to Acrylic Acid separation using low-volatility solvents includes the following:

U.S. Pat. No. 3,534,091 discloses the use of C6-C22 fatty carboxylic acids as extraction solvents for separating C3 and C4 carboxylic acids, including AA, from aqueous solutions. It describes the use of isooctanoic acid (i.e. 2-methyl heptanoic acid), among others, as the solvents. Example 5 teaches the use of isooctanoic acid to extract AA from a 1.135 wt % aqueous solution, with a 1:9 solvent:aqueous volumetric ratio. Example 1 used a 1:1 solvent:aqueous feed ratio, where the aqueous contained 0.864 wt % AA, and achieved an AA recovery of 54% to the extract.

U.S. Pat. Nos. 6,166,248 and 6,555,707 disclose the use of solvents such as lactams (methylpyrrolidone) or other organic acids such as 2-ethylhexanoic acid as an absorption solvent to remove AA from hot gaseous streams. The gas stream containing non-absorbed components is condensed into an acid water stream which is generally incinerated.

U.S. Pat. No. 6,281,386 discloses of the use of high boiling solvents, specifically claiming heavy solvents that are aromatic compounds with normal boiling points between 260° and 380° C. in the purification of acrylic acid.

SUMMARY OF THE INVENTION

C2 saturated and/or C3, and/or C4 saturated and/or unsaturated mono carboxylic acids, especially acrylic acid (AA), are recovered from dilute aqueous mixtures by liquid-liquid extraction with a solvent comprising an organic acid or ester or mixtures thereof, with a melting point below 10° C., a normal boiling point between 190 and 280° C., and a Hildebrand solubility parameter between 8 and 11 $cal^{1/2}$ $cm^{-3/2}$. The majority of carboxylic acid is transferred from the aqueous stream into the separate solvent phase. The carboxylic acid is then concentrated preferably by vacuum distillation, whereby the carboxylic acid is distilled out of the high-boiling solvent, yielding a concentrated solution of carboxylic acid, which may or may not contain water and/or other lower boiling organic species that were co-extracted into the solvent. The solvent, separated from the extract may be cooled and re-used for additional extraction. Polymerization inhibitors may be added to the carboxylic acid-solvent extract and/or at selected points in the concentration steps, to prevent the undesired polymerization of the carboxylic acids that can occur at high liquid concentrations or when subjected to heating. The extraction and/or the concentration steps may be carried out as either batch or continuous operations. The carboxylic acid can be purified from the concentrate by conventional means, e.g. those methods widely practiced in the commercial manufacture of high-purity products such as acrylic acid.

DETAILED DESCRIPTION OF THE INVENTION

Figure 1:
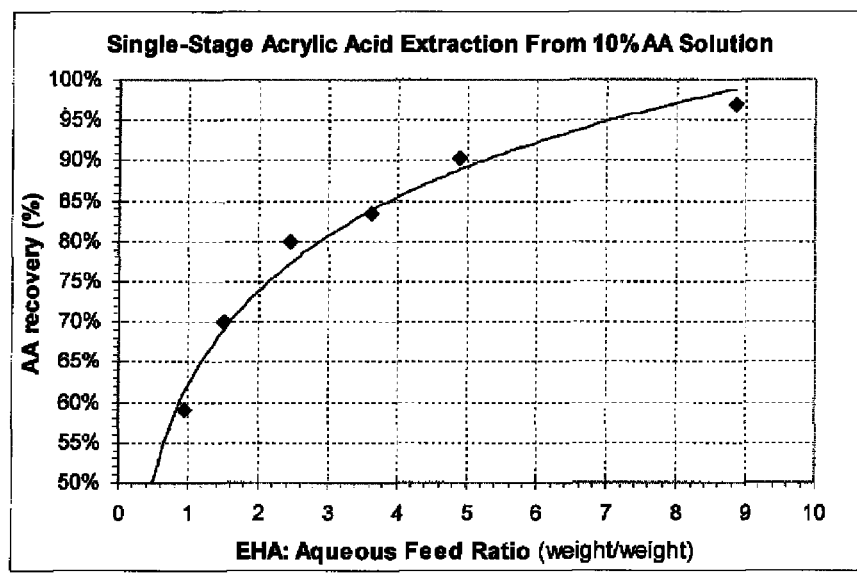
FIG. 1 is a plot of AA recovery versus EHA:Aqueous Feed Ratio for Examples 2-7.

The present invention is directed towards a method to recover and concentrate C2 saturated and/or C3, and/or C4 saturated and/or unsaturated mono carboxylic acids, especially acrylic acid, from dilute aqueous solutions. More particularly, the present invention is directed toward a method to recover C2 saturated and/or C3, and/or C4 saturated and/or unsaturated mono carboxylic acid from wastewater streams, as a concentrate that is compatible with established carboxylic acid purification systems.

Further, the present invention is directed towards a method to maximize the water removal from aqueous C2 saturated and/or C3, and/or C4 saturated and/or unsaturated mono carboxylic acids, especially acrylic acid, to minimize the energy requirements for the down-stream purification of the carboxylic acids. The method of the present invention achieves desired C2 saturated and/or C3, and/or C4 saturated and/or unsaturated mono carboxylic acid recovery and concentration at high overall recoveries of such carboxylic acids, i.e., minimizing losses to separation inefficiencies and formation of decomposition/degradation products.

In the method of the present invention C2 saturated and/or C3, and/or C4 saturated and/or unsaturated mono carboxylic acids, especially acrylic acid (AA), are recovered from dilute aqueous mixtures by liquid-liquid extraction with a solvent comprising an organic acid or ester or mixtures thereof, with a melting point below 10° C., a normal boiling point between 190° and 280° C., and a Hildebrand solubility parameter between 8 and 11 $cal^{1/2} cm^{-3/2}$. In the extraction, the majority of the carboxylic acid is transferred from the aqueous stream into the separate solvent phase. The solvent phase containing the carboxylic acid is then concentrated by distillation. The carboxylic acid is distilled out of the high-boiling solvent, yielding a concentrated solution of carboxylic acid, which may or may not contain water and/or other lower boiling organic species that were co-extracted into the solvent.

The carboxylic acid-lean aqueous raffinate can either be recycled, e.g. for absorption of additional carboxylic acid, or disposed of, or treated in an appropriate manner.

The solvent, separated from the extract may be cooled and re-used for additional extraction.

The carboxylic acid can be purified from the concentrate by conventional means, e.g. those methods widely practiced in the commercial manufacture of high-purity products such as acrylic acid.

The extraction and/or the concentration steps may be carried out as either batch or continuous operations. The extraction unit may be either a column-type unit, or a series of discrete mixers and liquid-liquid separators, or centrifugal-type liquid-liquid extractors. The column-type units are preferred, and may be of any of the configurations known to those skilled in the art of liquid-liquid extraction. The extractor may be operated as either aqueous-phase continuous/solvent dispersed, or solvent-phase continuous/aqueous dispersed.

The solvent extraction is preferably carried out in a continuous counter-current liquid-liquid extractor column configured to provide the equivalent of 3 or more theoretical stages of contacting. The extractor column may be of any suitable configuration known to those skilled in the art of liquid-liquid extraction.

The ratio of solvent to aqueous feed may be more or less than in the examples cited. The preferred range of solvent: aqueous feed ratios are 0.8:1 to 2:1 by weight. It is clear to those skilled in the art of liquid-liquid extraction that the solvent:aqueous feed ratio required is dependent on the concentration of carboxylic acid in the aqueous feed, the number of and configuration of extraction stages, and the desired % recovery of the carboxylic acid.

The extraction may be carried out at temperatures between the freezing point and boiling point of aqueous phase at the operating pressure of the extractor. Since the solvents have low volatility, it is desirable to operate the extraction near ambient pressure, to minimize the required design pressure and associated equipment cost. The preferred temperatures for the extractions represent a trade-off or optimization between higher temperatures, which facilitate easier phase separation, and lower temperatures, which favor higher extraction efficiencies and reduced solvent losses due to solubility in the aqueous raffinate. When the extractions are run at elevated temperatures, solvent losses can be minimized by post-cooling the raffinate to reduce the solvent solubility, and then recovering (e.g. by decantation) and recycling the additional solvent that phases separates at the lower temperature.

The preferred carboxylic acid extraction solvents are 2-ethyl hexanoic acid (EHA), dibutyl phthalate (DBP), methyl benzoate (MBZ), ethyl benzoate (EBZ), or mixtures thereof. The ratio of solvent to aqueous feed preferably ranges from about 0.5:1 to 4:1 by weight.

The concentration of the carboxylic acid is preferably accomplished by vacuum fractional distillation, most preferably at the deepest vacuum consistent with the ability to condense the carboxylic acid-rich distillate using convenient and inexpensive cooling media, e.g. cooling water or air cooling.

AA and other unsaturated carboxylic acids are reactive and thermally sensitive monomers. They readily polymerizes spontaneously at high concentrations even at ambient conditions, and at lower concentrations when subjected to moderate heating. It is normal practice to add polymerization inhibitors to processes and liquid streams containing AA or other unsaturated carboxylic acids. Several classes of inhibitors are widely used. The most commonly used inhibitors require the presence of low concentrations of oxygen to "activate" the inhibitors. In the absence of oxygen, AA or other unsaturated carboxylic acids can still polymerize, even with the inhibitor present. However, other inhibitors are available that are effective, even in the absence of oxygen.

Polymerization inhibitors, such as those known to those skilled in the art of unsaturated carboxylic acid purification, may be added to the carboxylic acid-solvent extract and/or at selected points in the concentration steps, to prevent the undesired polymerization of (unsaturated) carboxylic acids (such as AA) that can occur at high liquid concentrations or when subjected to heating. When polymerization inhibitors are used, it is preferable to use the class of inhibitors that do not require the presence of oxygen to be active, simplifying the inerting requirements to ensure that the vapors do not become flammable mixtures.

In a preferred embodiment of the invention, the carboxylic acid to be recovered is acrylic acid (AA), especially where the AA is produced by the oxidation of propylene or propane to acrolein and its subsequent further oxidation to AA, and the solvent is selected from EHA, DBP, MBZ, or EBZ. The extraction is carried out in a continuous counter-current liquid-liquid extractor with at least three theoretical extraction stages, using at least 1:1 solvent:aqueous feed by weight. The extraction is most preferably carried out at a temperature between 35° and 55° C., to facilitate the rapid separation of the two liquid phases. The concentration of the recovered AA is accomplished by fractional distillation. The AA concentrate that is produced as the overhead distillate product is sent to an AA purification facility. The substantially AA-free EHA bottoms product from distillation is cooled and recycled to the extractor. A feed/bottoms heat exchanger is used to preheat the distillation feed and pre-cool the recovered EHA, to reduce the heating requirements for distillation and cooling requirements for EHA recycle.

In another preferred embodiment of the invention, the concentration of the recovered carboxylic acid is accomplished by fractional distillation under vacuum, wherein the operating pressure (vacuum) is as low as possible, consistent with the ability to condense the concentrated carboxylic acid overhead distillate product using low cost cooling media such as cooling water or air cooling. This serves to minimize the temperatures throughout the distillation, allowing the use of lower-temperature heating media, as well as minimizing the likelihood of thermal degradation or polymerization.

In an alternate preferred embodiment of the invention, the aqueous carboxylic acid feeds are dilute AA streams normally considered to be wastewater from acrolein produced by the oxidation of propylene, wherein the AA is a non-selective byproduct of the acrolein reaction. The extraction solvent is EHA. AA extracted into the EHA solvent is separated and concentrated by vacuum distillation. The AA concentrate resulting from extraction of acrolein-process wastewater contains substantially the same impurities as AA made by well-established commercial practice of 2-stage oxidation of propylene to acrolein, which is further oxidized to AA. Hence the AA concentrate is similar in composition to the crude AA made in AA production facilities, and may therefore be readily blended with normal crude AA for purification to yield high-purity AA.

In an alternate embodiment of the invention, the carboxylic acid is crude aqueous AA from conventional AA manufacture by the oxidation of propylene, wherein the AA is selectively produced in a gas phase reactor, and recovered from the reaction gases by absorption into water. The extraction solvent is EHA. AA extracted into the EHA solvent is separated and concentrated by vacuum distillation. If the extraction and concentration steps are carried-out under conditions that maximize the separation of AA from the water used in absorption, the concentrated AA may have a sufficiently lower water content to facilitate simpler and less energy-intensive means of purifying the AA, compared to the conventional AA purification methods such as multi-column extractive distillation.

In an alternate embodiment of the invention, polymerization inhibitors are added at suitable points in the process, e.g. to the extract prior to being sent to the concentration (distillation) equipment; at the inlet to the distillate overhead condenser; etc. If the inhibitors (e.g. quinones) require that oxygen be present to activate the inhibitor, oxygen-poor air may be admitted into the concentration equipment, provided that the vapors are maintained at oxygen concentrations below the flammability limits of the solvent. It is most preferable to use inhibitors (e.g. phenothiazine) that do not require the presence of oxygen to be effective; this allows the concentration equipment to be operated without the introduction of external gases.

EXAMPLES

The following examples provide details wherein the carboxylic acid is acrylic acid (AA). However, while the subject invention is especially well suited for AA recovery and concentration using EHA as a solvent, it is not intended to limit its applicability to these materials. It should be apparent to those skilled in the art that the subject invention is applicable to other carboxylic acids, e.g. acetic acid, propionic acid, butyric acids, methacrylic acid, etc.

In the examples below, single-stage extractions were performed at ambient pressure by shaking dilute aqueous AA solutions (AAAS) with the solvent in a glass separatory funnel, and then allowing the liquid phases to separate. The aqueous and organic layers were decanted and weighed. The two phases were analyzed to determine the AA extraction efficiency and the partitioning of the other organic species.

Example 1

Single-Stage AA Extraction from Acrolein Process Wastewater Using EHA as the Solvent The aqueous AA solution was a wastewater stream from an acrolein manufacturing process containing the following (compositions given in weight %; the balance is water).

| | |
|---|---|
| Acrylic Acid | 7.23% |
| Maleic acid | 1.05% |
| Acetic Acid | 1.36% |
| Allyl Alcohol | 0.07% |
| Acrolein | 0.06% |
| Acrolein dimer | 0.04% |

The solvent used was 2-ethylhexanoic acid from Alfa Aesar. Initial trails at ambient temperature resulted in a quasi-emulsified mixture which only partially separated; an intermediate "rag" layer remained. It was found that subsequent heating of the mixture to 45°-50° C. allowed the two liquid phases to separate cleanly after several minutes. Using a 1.6:1 EHA:Aqueous feed weight ratio at 50° C. resulted in 73% recovery of AA to the organic phase.

Examples 2-7

Single-Stage AA Extraction from Water Using EHA as the Solvent

Aqueous AA solutions, 10 wt % AA in distilled water were contacted with EHA solvent. Single-stage extractions were run at approximately 50° C. Six EHA:Aqueous feed mass ratios were run, ranging from 1:1 to 9:1. The partitioning of AA between the resulting 2 liquid phases and mass balances were determined. The results are shown in Table 1, and plotted in FIG. 1.

TABLE 1

| Example | 2 | 3 | 4 | 5 | 6 | 7 |
|---|---|---|---|---|---|---|
| EHA:Aqueous Feed Ratio | 1.0 | 1.5 | 3.6 | 2.5 | 4.9 | 8.9 |
| Average AA recovery to Extract | 59% | 70% | 83% | 80% | 90% | 97% |

In the following examples, the process conditions and material balances were determined by computer simulation, using the Aspen Plus process simulator, with the non-random two-liquid (NRTL) thermodynamic model used to calculate mixture properties, component separations, etc. The NRTL component binary pair parameters were based on values regressed from literature and experimental data, where available, and predicted using the Aspen "PCES" property component estimator (based on "UNIFAC" group contribution method) for binary pairs for which data was not available.

Example 8

Countercurrent Multi-Stage AA Extraction from Acrolein Process Wastewater

Figure 2:
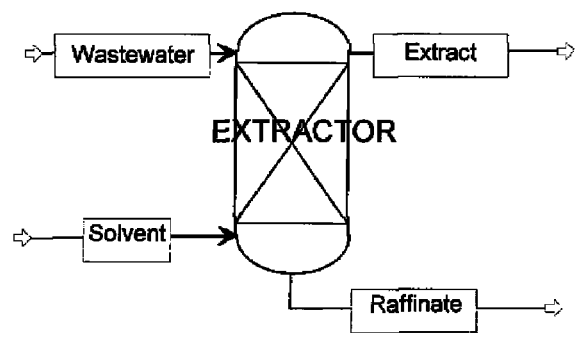
FIG. 2 is a process flow sheet for Examples 2-7.
Figure 3:
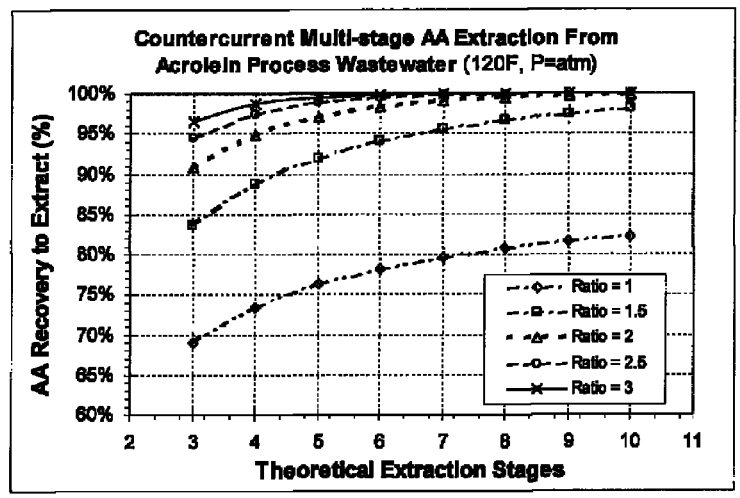
FIG. 3 is a plot of AA recovery versus Theoretical Extraction Stages for example 8.

A simulation was run of contacting the wastewater stream of Example 1 counter-currently with EHA in an extraction column providing several theoretical stages of contacting. The column operating at ambient pressure. The simulation had the wastewater fed to the top of the column, and the EHA solvent fed to the bottom of the column. The solvent-rich extract exited the top of the column, and the denser water-rich raffinate exited the bottom of the column. The wastewater feed stream was at 120° F.; the EHA solvent feed temperature is 120° F. The process flowsheet is depicted schematically FIG. 2. The number of theoretical extraction stages was varied, from 3 to 10. The % recovery of acrylic acid (acrylic acid extracted from the feed into the solvent extract) vs. the number of theoretical extraction stages for solvent to feed weight ratios of 1:1, 1.5:1, 2:1, 2.5:1 and 3:1 were run. The results are shown in FIG. 3.

Example 9

AA Concentration by Vacuum Distillation from the EHA Extract, with EHA Recycle to Extraction A simulation was run of contacting the wastewater stream of Example 1 counter-currently with EHA-rich solvent, in an extraction column as described in Example 8, provided with the equivalent of 6 theoretical stages of contacting. The wastewater was fed to the top of the column, and the EHA solvent was fed to the bottom of the column. The solvent-rich extract exited the top of the column, and the denser water-rich raffinate exited the bottom of the column. A ratio of solvent: aqueous feed to the extractor of 1.8:1 by weight was used.

Figure 4:
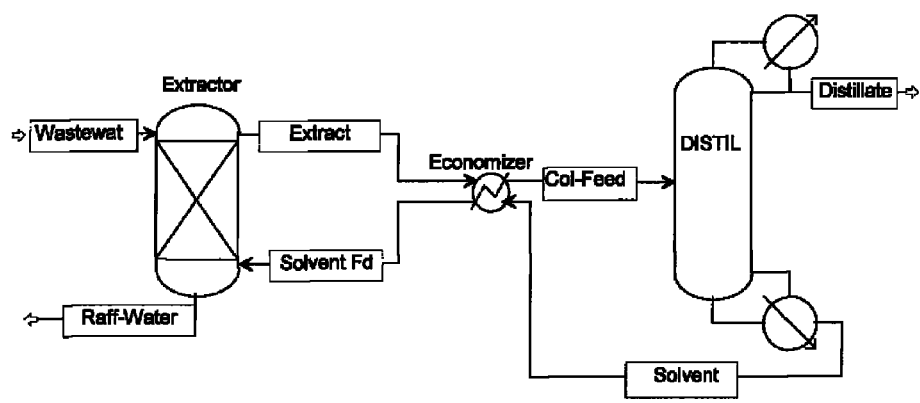
FIG. 4 is a process flow sheet for Example 9.

The EHA extract was sent to a vacuum distillation column, provided with 15 theoretical stages (including the condenser and reboiler), with the feed on the 9th theoretical stage from the top. AA, water, and other co-extracted components would go to the overhead distillate product, while the substantially AA-free EHA is recovered as the bottoms product. Sufficient inhibitor was added as a solution in AA, to the column via the inlet to the condenser to maintain 100 ppm inhibitor in the concentrated AA distillate. The column operated at a 1.75 reflux ratio. The overhead pressure was 100 torr. The feed to the column was pre-heated by cross-exchanging with the hot bottoms. The EHA bottoms was subsequently cooled to the extraction temperature of Example 8, and recycled to the extractor. Make-up EHA solvent, to compensate for the amount saturating the aqueous raffinate, was added, to maintain the desired solvent ratio. The process flowsheet is depicted schematically in FIG. 4. At these conditions, the partitioning of the components between the extract and the aqueous raffinate is as follows:

|  | Extract | Raffinate |
|---|---|---|
| Acrylic Acid | 97.2% | 2.8% |
| Maleic Acid | 26.4% | 73.6% |
| Acetic Acid | 79.6% | 20.4% |
| Allyl Alcohol | 61.8% | 38.2% |
| Acrolein | ~100% | traces |
| Acrolein dimer | 35.5% | 64.5% |

The extract also contains 1.6 wt % water.
The concentrated AA distillate contains 60 wt % AA, 33.3% water, 10 ppm EHA, with the balance being other organics compounds that co-extracted with the AA. The EHA bottoms is nearly pure, containing 1000 ppm maleic acid, 3 ppm AA and 135 ppm inhibitor.

Example 10

DBP as the Extraction Solvent

A simulation was run substantially the same as Example 9, except that dibutyl phthalate (DBP) was the extraction solvent. Because DBP is denser than water, the solvent was fed to the top of the extractor, and the aqueous layer was fed to the bottom of the extractor; the extract was drawn from the bottom of the extractor, and the raffinate was drawn from the top of the extractor. A ratio of solvent:aqueous feed to the extractor of 1.4:1 by weight was used. The EHA extract was sent to a vacuum distillation column, provided with 7 theoretical stages (including the condenser and reboiler), with the feed on the 3rd theoretical stage from the top. At these conditions, the partitioning of the components between the extract and the aqueous raffinate is as follows:

|  | Extract | Raffinate |
|---|---|---|
| Acrylic Acid | 99.3% | 0.7% |
| Maleic Acid | 28.2% | 71.8% |
| Acetic Acid | 56% | 44% |
| Allyl Alcohol | 27.7% | 72.3% |
| Acrolein | ~100% | ~0% |
| Acrolein dimmer | 28.2% | 71.8% |

The extract also contained 1.8 wt % water.
The concentrated AA distillate contained 63.7 wt % AA, 31.7% water, 10 ppm DBP, with the balance being other organics compounds that co-extracted with the AA. The DBP bottoms were nearly pure, containing traces of AA, 100 ppm inhibitor, and 1000 ppm maleic acid.

Example 11

MBZ as the Extraction Solvent

A simulation was run substantially the same as Example 9, except that methyl benzoate (MBZ) was the extraction solvent. Because MBZ is denser than water, the extractor feed and take-off configuration was the same as in Example 10. A ratio of solvent:aqueous feed to the extractor of 1:1 by weight was used. The EHA extract was sent to a vacuum distillation column provided with 17 theoretical stages (including the condenser and reboiler), with the feed on the 6 theoretical stage from the top.

At these conditions, the partitioning of the components between the extract and the aqueous raffinate was as follows:

|  | Extract | Raffinate |
|---|---|---|
| Acrylic Acid | 98.2% | 1.8% |
| Maleic Acid | 39.1% | 60.9% |
| Acetic Acid | 71.1% | 28.9% |
| Allyl Alcohol | 25.5% | 74.5% |
| Acrolein | ~100% | ~0% |
| Acrolein dimer | 39.1% | 60.9% |

The extract also contains 4.8 wt % water.

The concentrated AA distillate contained 47.6 wt % AA, 48.1% water, 900 ppm MBZ, with the balance being other organics compounds that co-extracted with the AA. The MBZ bottoms were nearly pure, containing 997 ppb AA, 250 ppm inhibitor, and 2000 ppm maleic acid.

While the present invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A method for separating acrylic acid and/or aldehydes from aqueous solutions by extraction wherein the improvement comprises using as the extractant an organic acid or ester or mixtures thereof with a melting point below 10° C., a normal boiling point between 190° and 280° C. and a Hildebrand solubility parameter between 8 and 11 $cal^{1/2} cm^{-3/2}$ and separating said extractant from said mono carboxylc acid via a thermal separation process.

2. The method of claim 1 wherein said extractant is selected from the group consisting of 2-ethyl hexanoic acid, methyl benzoate, ethyl benzoate and mixtures thereof.

3. The method of claim 1 wherein said aldehydes are selected from the group consisting of acrolein, acetaldehyde, methacrolein, propionaldehyde, butyraldehyde, crotonaldehyde, 3-butenal, and mixtures thereof.

4. The method of claim 1 further comprising adding polymerization inhibitors to the extractant.

5. The method of claim 1 wherein said aqueous solution comprises less than about 10% by weight of said carboxylic acids and/or acrolein.

6. The method of claim 1 wherein said extractant to aqueous solution ratio is from about 0.5 to 1 to about 4 to 1 by weight.

* * * * *